United States Patent [19]

Lilaonitkul

[11] 4,276,881
[45] Jul. 7, 1981

[54] COMPACT TAMPON APPLICATOR

[75] Inventor: Amnuey Lilaonitkul, Appleton, Wis.

[73] Assignee: Kimberly-Clark Corporation, Neenah, Wis.

[21] Appl. No.: 86,810

[22] Filed: Oct. 22, 1979

[51] Int. Cl.³ .............................................. A61F 15/00
[52] U.S. Cl. .................................................... 128/263
[58] Field of Search ................ 128/263, 285, 264, 270

[56] References Cited

U.S. PATENT DOCUMENTS

| | | | |
|---|---|---|---|
| 3,101,713 | 8/1963 | Sargent | 128/263 |
| 3,895,634 | 7/1975 | Berger et al. | 128/263 |

FOREIGN PATENT DOCUMENTS 700840 12/1964 Canada ...................................... 128/263

*Primary Examiner*—John D. Yasko
*Attorney, Agent, or Firm*—Howard Olevsky; William D. Herrick

[57] ABSTRACT

A tampon applicator is provided with an inner and an outer sleeve. The inner sleeve extends slightly beyond the outer sleeve when the sleeves are mated and is only slightly longer than the tampon for which the applicator is designed to deliver. In one embodiment, the inner sleeve has a series of slots tapering inward and downward from the forward end which are designed to engage injection guides located on the inner surface of the outer sleeve near the base.

9 Claims, 13 Drawing Figures

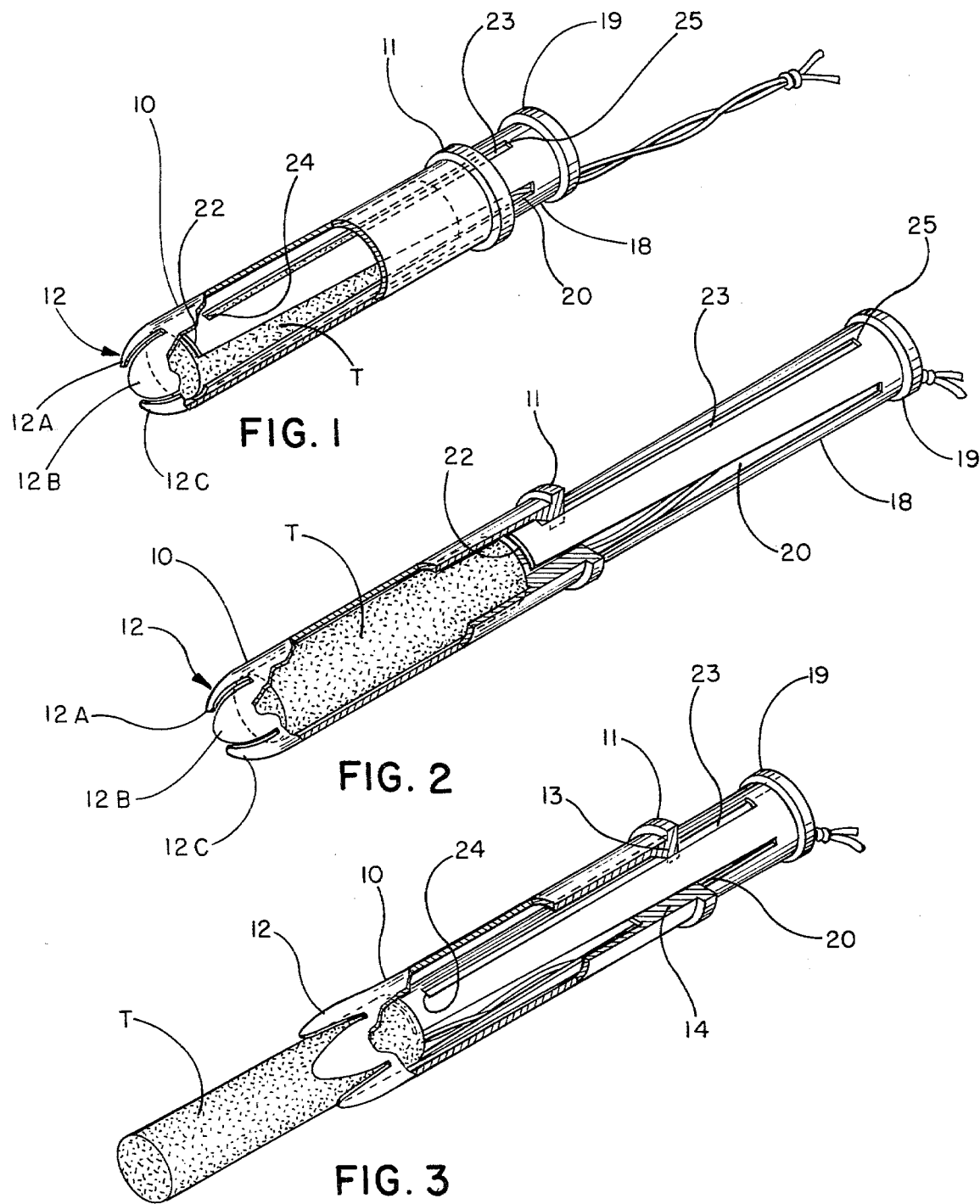

COMPACT TAMPON APPLICATOR

FIELD OF THE INVENTION

The invention relates to a tampon applicator. Particularly it relates to a telescoping tampon applicator of reduced length.

BACKGROUND OF THE INVENTION

Tampons are a preferred method for absorbing menstrual fluid by many women because, among other reasons, they are traditionally more portable than sanitary napkins.

While the tampons themselves are only a couple of inches long, when they are inserted in the traditional tube-type applicators, the applicators add substantially to the length of the tampon so that the composite may be three or four inches or more in length. The tampon applicator is long enough so that it cannot easily be carried in the woman's hand without a portion of it being exposed, resulting in some social embarrassment.

Another problem is associated with the insertion of the tampon, and that is the friction encountered during periods of low flow at the forward edge of the tampon material. As a result, several tampon applicators have been designed which have an outer tube hemispherically shaped or bullet shaped at the leading edge, which enclose the tampon prior to insertion and are made of a smooth-surfaced material having less frictional drag than the tampon itself. They flex open upon the application of pressure from the bottom of the applicator. Examples of these tampons can be found in U.S. Pat. Nos. 3,807,399; 3,830,236; 3,895,634; 3,983,868; 2,754,822; 3,015,332; 3,204,635; 3,433,225; 3,581,744; 3,628,533; 3,696,812; 3,699,962; and 3,765,416. As is taught in several of these patents, one type of application is that a cylindrical tampon of substantially equal diameter along the length of the cylinder is inserted through the forward or leading edge of the outer sleeve of the applicator during assembly where the individual segments are projectedly straight or open. After insertion these approximately triangular-shaped segments at the forward edge of the applicator are thermo-mechanically closed to provide the hemisphere or bullet-shaped outer surface. A separate, inner portion of the applicator extends from the bottom or rearward portion of the applicator and, when pressure is applied on the bottom of this inner portion, somewhat in the manner of a hypodermic syringe, the forward part of the inner portion pushes against the base of the tampon forcing the leading edge of the tampon out through the forward edge of the outer tube of the applicator. Other types of applicators have the segments at the forward edge closed in an arcuate shape prior to assembly. The tampon is loaded from the rearward end of the applicator.

U.S. Pat. No. 3,101,713 issued to D. O. Sargent describes a telescoping tampon applicator having an inner tube or sleeve and an outer sleeve. The outer sleeve of the tampon applicator has shoulders located at a portion of the inner surface approximately midway along its length. The shoulders are designed to retain the inserted tampon within the forward portion of the outer tube of the tampon applicator. The outer tube also has, at the inner surface, guides which taper toward the base from a portion near the midpoint of the length of the outer tube. These guides are designed to engage slots which extend from the forward edge of the inner tube to a point approximately halfway down the length of the tube. Other slots on the inner tube are designed to mate with the shoulders of the outer tube with these slots having stops located near the forward and the rearward portion of the inner tube. The concept of this particular delivery system is that when the composite is assembled the tampon rests on the shoulders of the outer tube which also surrounds the inner tube so that the inner tube, mating as indicated with the outer tube, also surrounds the tampon. For insertion the inner tube is pulled backwards, the tampon which must be radially expandable, radially expands so that it abuts the inner surface of the outer tube. The inner tube which has been slid backward so that it is extended as far as possible in relation to the stop mechanism described above, is then pushed forward to deliver the tampon. This is possible because the tampon after removal of the inner tube cannot slide backward farther than the stops and, as it is radially expanded its outer edges expand so that they are in alignment with the leading edge of the inner sleeve.

There are difficulties inherent in the Sargent approach however. First, as mentioned, it is particularly desirable that the outer sleeve of the tampon applicator be made of a smooth plastic. Conventionally these plastics are moldable and are shaped around a mandrel. The utilization of the tampon supports midway along the inside of the outer sleeve would be impossible to construct by conventional high speed plastic molding techniques utilizing a mandrel. In addition, the delivery system depends upon the radial expansion of the tampon resulting from compression. In the dry state, tampons are slow to radially expand especially when they have been substantially compressed and therefore actual delivery of the tampon after the applicator has been inserted may not be accomplished.

Also, even though mating sleeves are used for this particular tampon, due to the particular construction features of the outer sleeve, i.e. particularly the tampon abutment portions on the inner surface, the applicator as assembled in the closed position is approximately twice as long as the tampon itself thereby not substantially reducing the overall length of the applicator-tampon combination.

The subject application is designed to overcome the disadvantages inherent in Sargent by producing a tampon applicator, having, in one embodiment, a plastic outer tube with an arcuate leading edge; the applicator being of substantially reduced length and capable of delivery of a tampon which need not be radially expandable.

SUMMARY OF THE INVENTION

The outer tube of the tampon applicator of this invention has as one of its essential components an injection guide positioned near the rearward end of the inner surface of the outer tube. This injection guide is widest near the base, has an abutment surface which prevents removal of the inner tube and tapers inwardly to a point slightly above the base. The injection guide is designed to cooperate with a radially compressible inner tube, which, in one embodiment is a series of slots extending taperingly from the leading or forward edge of the inner tube to a stop portion near the base. The compressibility of the inner tube is critical to the subject invention.

By taper in this context it is meant that the width of the slots near the top portion be narrower than that at the open portion at the forward end of the inner tube.

In a particularly preferred aspect of the subject invention, the outer tube is made of a friction-lessening material such as plastic or cardboard having an arcuate configuration formed by a series of triangular petals at the forward edge of the outer tube. When this particular outer tube configuration is utilized, the injection guide is located at the inner surface of the outer tube near the bottom portion of the tube and slots designed to engage the injector guide are situated in the inner tube. The injector guide engaging slots have stops near the forward and rearward ends of the tube.

The mechanism of the subject invention can be more easily understood by reference to the drawings in which:

FIG. 1 is a perspective view of the tampon applicator of this invention.

FIG. 2 is a view of the assembly of the plunger also in perspective in which the inner tube has been pulled rearward prior to injection.

FIG. 3 is a perspective view of the tampon applicator with the tampon substantially ejected during delivery.

FIG. 1 shows the closed tampon applicator with the tampon T indicated in phantom lines. As can be seen the tampon is only slightly shorter than the length of the composite applicator in the closed position. As such it is easily concealed in the palm of the hand. The outer tube as depicted therein shows a forward or leading edge 12 and a finger abutment 11 used in conjunction with ring 19 on the inner tube for ease of insertion.

Figure 4:
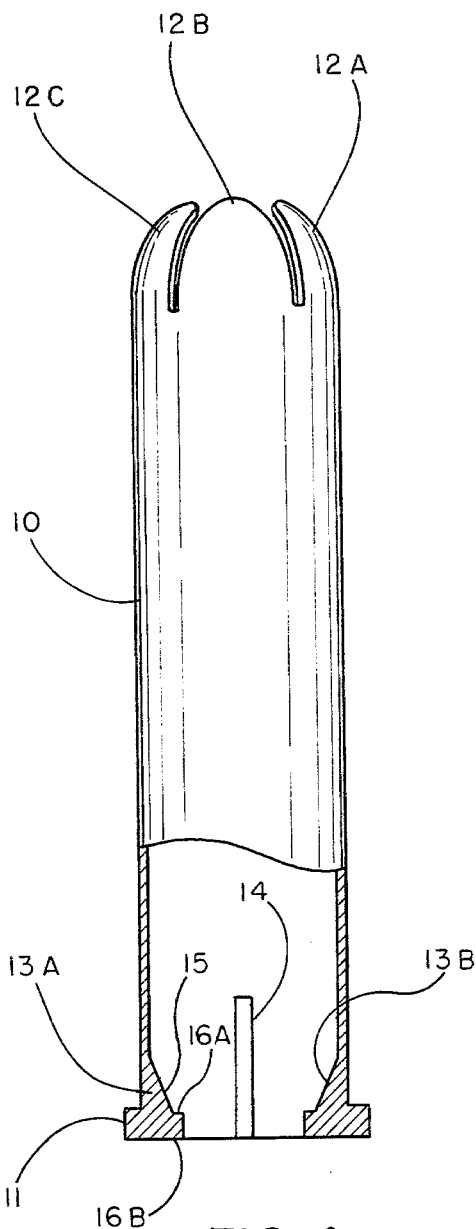
FIG. 4 is a cross section taken along the longitudinal axis of the outer tube.
Figure 10:
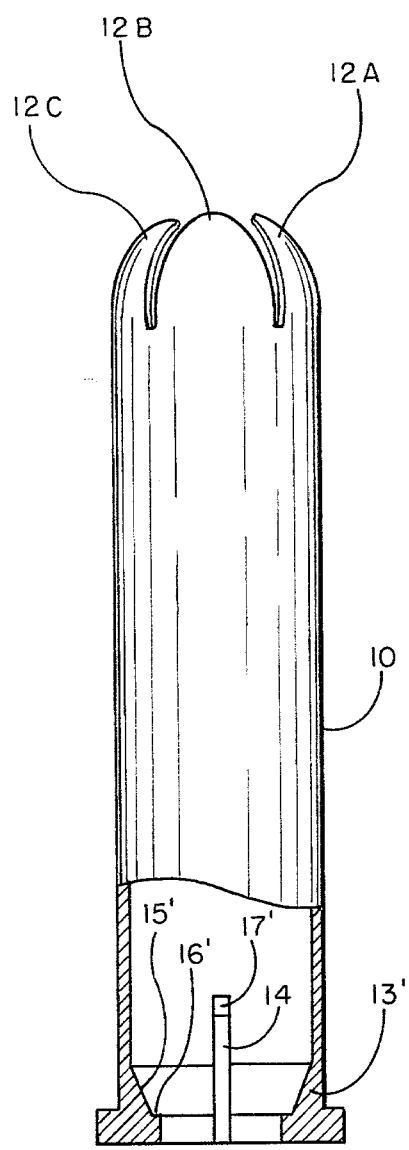
FIGS. 10-13 are views corresponding to FIGS. 4-7 of another embodiment of this invention.
Figure 11:
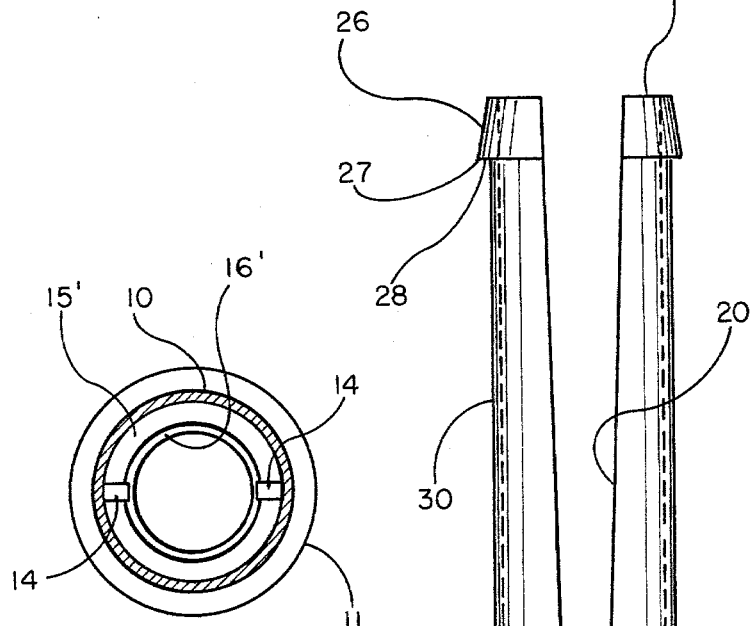
Figure 12:
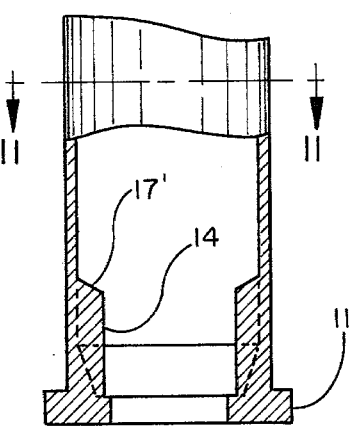
Figure 13:
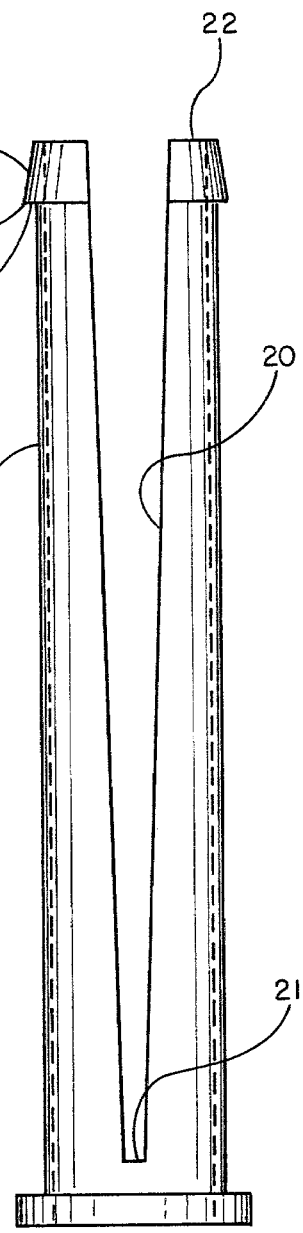

The tampon and applicator are mated by insertion through the leading edge 12 of the outer tube 10 by conventional means. The outer tube 10 as illustrated in FIGS. 4 and 10 shows the petals 12A, 12B and 12C. It should be noted that two other identical petals are present at the leading edge but are not illustrated in these figures.

Figure 7:
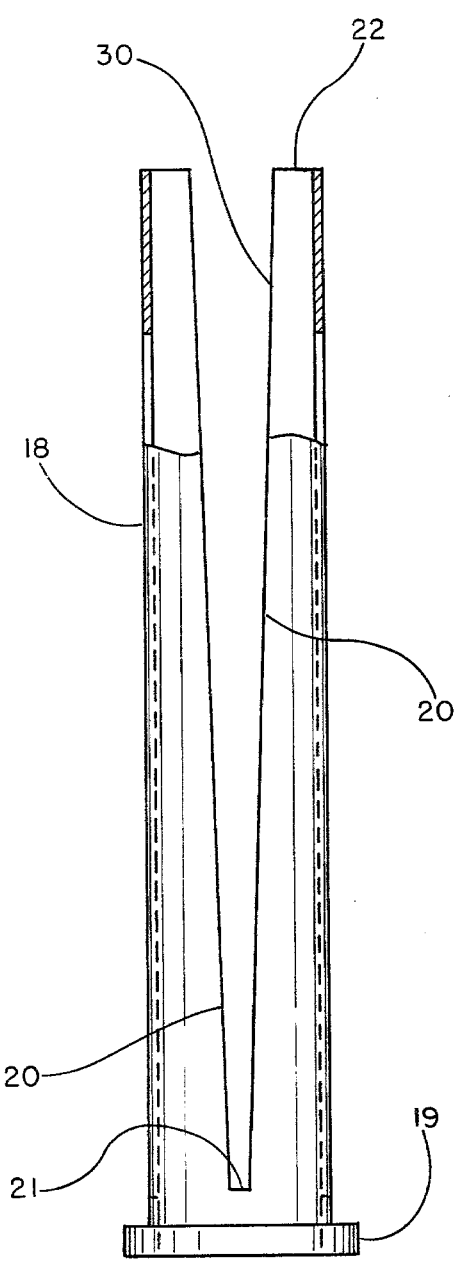
FIG. 7 is a side view of the inner tube of this invention.
Figure 8:
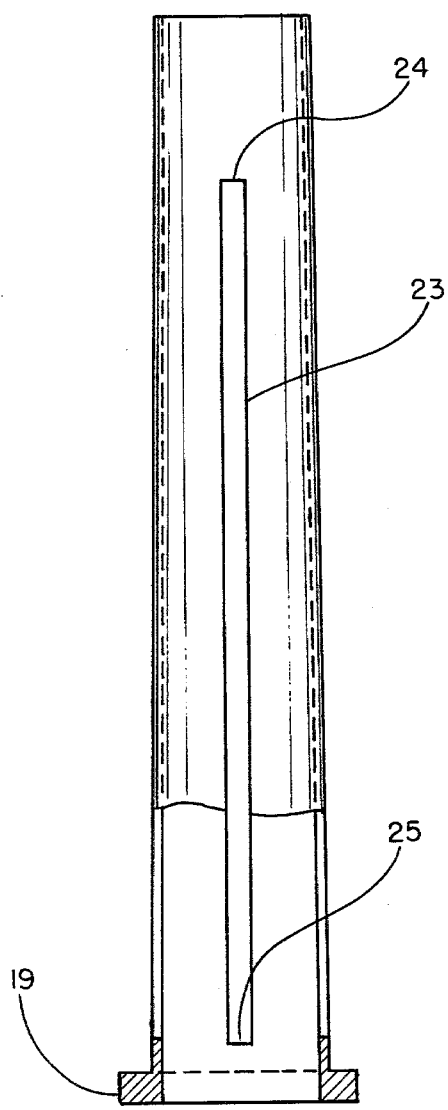
FIG. 8 is a side view taken along a longitudinal axis of the inner tube after a 90° rotation of FIG. 7.

As can be seen in FIGS. 2, 7 and 8 the inner tube has two series of slots 20 and 23. The length and spatial relationship of the slots to the remainder of the inner tube 18 can best be seen by reference to FIGS. 7 and 8. The frontward and rearward stops 24 and 25 respectively of slots 23 are shown at FIG. 8. These stops are designed to engage injector guide 13. The upper face at the base of the injector guides 16A of the outer sleeve shown in FIG. 4 is designed to abut the stop 24 at the forward edge of slot 23; while the bottom face 16B is designed to abut stop 25 depending upon the relative position of the inner and outer sleeves.

Figure 5:
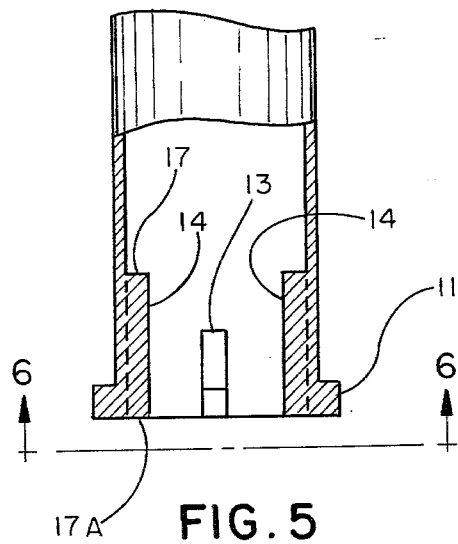
FIG. 5 is a cross section taken along the longitudinal axis of the outer tube after a 90° rotation of FIG. 4.

Referring to FIGS. 5 and 7, the tapered slot 20 engages the shoulder 14 such that the stop 21 at the bottom of the tapering slot 20 abuts face 17A of the shoulder 14 when the tubes are matingly inserted and the tampon is present as shown in FIG. 1. The shoulders are served as a stop for the tampon when the inner tube is pulled rearward during the tampon delivery process.

Figure 6:
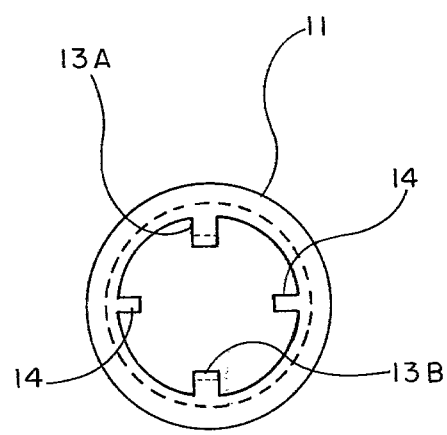
FIG. 6 is a cross sectional view of the bottom of the outer tube of FIG. 4.

As can be seen from FIGS. 4 and 6 the injector guides for this embodiment are characterized by two separate identical extensions 13A and 13B.

The spatial relationship of the injector guides and the shoulders can be seen in FIG. 6. As the inner tube is pulled rearward, the injector guides 13A and 13B slide along the corresponding slots in the inner tube 23. As shown in FIG. 2, the tampon T (shown in phantom lines as in FIG. 1) is positioned exactly as in FIG. 1 but the inner tube during rearward withdrawal has been compressed by the tapering contact of stop 24 with the sloping surface 15 of the injector guide so that the diameter of the forward edges of the inner tube of flange 30 as shown in FIG. 7 is less than the starting diameter prior to the withdrawal of the inner tube. The forward edge of flange 30 with the reduced diameter has less diameter than the base of the tampon. As a result, when the inner tube has been extended so that the stop 24 engages the abutment surface 16A of the injector guide, the diameter at the forward edge is at its narrowest point and is less than that of the diameter of the base of the tampon. The surface 16A also prevents disengagement of the inner and outer tube.

The inner tube 18 is then pushed forward by grasping the ring 11 in a traditional manner and the tampon is delivered by the mechanism of the inner tube being returned to its engaged mating position with the outer tube.

As can be seen, the tubes need only be slightly longer than the tampon itself and the length of the tampon in fact governs the length of the applicator system.

Figure 9:
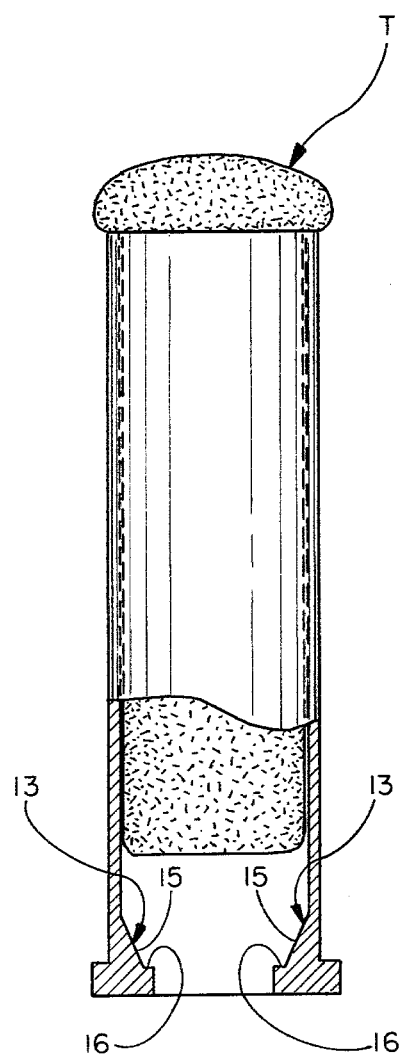
FIG. 9 is a longitudinal cross section of another embodiment of the subject invention showing the outer tube and the tampon.

FIG. 9 shows another embodiment of the subject invention with like parts being numbered in like manner. In this particular figure, the tampon has a mushroom shaped top and extends over the sides of the outer tube of the applicator. The tampon itself provides the leading edge during insertion and, since there is no problem with the tampon sliding back in the tube when the inner tube is withdrawn, the shoulders 14 which traditionally form a stop in the other embodiment are not needed. The particular advantages to this embodiment are related to ease and simplicity of manufacture of the outer tube and a further reduction on the total length of the tampon assembly due to the elimination of petal segments at the forward end.

Of course, it is possible to have an outer tube with shoulders 14 and an open leading edge and such an embodiment within the scope of this invention, although not illustrated. In this case there is no need for a mushroom-shaped pledget as shown in FIG. 9.

FIGS. 10-13 show an alternative design of the two-piece applicator assembly which will function similarly to that depicted in FIGS. 1-7. In this embodiment the original pair of injection guides 13A and 13B are replaced by circumferentially continuous guide 13' except where separated by a pair of shoulders 14. A gradual narrowing of the inside diameter of the tube is illustrated by slope face 15'.

The inner tube in this embodiment contains only two slots or grooves 20. The original slots 23 are eliminated. However, the inner tube has an additional fin 26 extended circumferentially near the front edge 22. This fin 26 has the leading edge 27 which is always in contact with the inner surface of the outer tube. As the inner tube is pulled rearward, leading edge 27 will catch the slope 15' resulting in a decreasing diameter of the front end 22. The pulling action will cease at the point when surface 28 of the fin is abutting surface 16' of the injection guide.

It is particularly apparent that the basic concept of the subject invention is the utilization of a compressible inner tube and a means for compressing it during withdrawal from the outer tube so that the inner tube at its leading edge of reduced diameter can be used to provide a means for pushing against the tampon during discharge.

Other variants within the scope of the subject invention will readily suggest themselves to those with skill in the art.

What is claimed is:

1. A tampon applicator comprising in combination:
   an outer tube, having:
   a forward end for delivery of a tampon;
   a rearward end with an open base for receiving an inner tube;
   an inner surface; and
   injection guide means on said inner surface tapering inwardly longitudinally toward said forward end of said outer tube from an area substantially at said base to a situs slightly above said base; and
   an inner tube of substantially the same length of the outer tube and the tampon to be inserted by said applicator for slidable mating in said outer tube said inner tube having:
   a forward end and a rearward end corresponding to the forward and rearward ends of the outer tube when mated; and
   a radially compressible means at least at the forward end of said inner tube compressed by said injection guide means during withdrawal of the inner tube from the outer tube, comprising a pair of inwardly and downwardly tapering slots at either side of said flanges, said slots having stops located near the rearward edge of the inner tube.

2. The applicator according to claim 1 where the injection guide means are a pair of identical projections.

3. The applicator according to claim 1 where the injection guide means are substantially circumferentially continuous around the inner surface.

4. The applicator according to claim 1, 2 or 3 in which the outer sleeve of the applicator is completely open at its outer end after tampon introduction.

5. The applicator according to claim 1, 2 or 3 in which the forward end of the outer sleeve of the applicator has a plurality of flexible triangular segments which form an arcuate leading edge when closed.

6. The applicator according to claim 1 or 2 wherein an injector guide engages a corresponding slot in said inner tube said slot having a stop near the forward edge of the inner tube.

7. The applicator according to claim 1, or 2 in which the outer tube has at least one shoulder and said inner tube has at least one slot engageable with said shoulder, said shoulder designed to support the tampon after the tampon is placed in said inserter.

8. The applicator according to claim 3 in which the radially compressible means are a pair of flanges having downwardly and outwardly directed fins at their forward edges and a pair of inward and downwardly tapering slots at either side of said flanges, said slots having stops located near the rearward edge of the inner tube.

9. A tampon applicator comprising in combination:
   an outer tube having a forward end for delivery of a tampon; a rearward end with an open base for receiving an inner tube; an inner surface having a pair of injection guides tapering inwardly longitudinally toward said forward end from an area substantially at said base to a situs slightly above said base; and in which said forward end has a plurality of flexible triangular segments which form an arcuate leading edge when closed;
   an inner tube of substantially the same length of the outer tube and of the tampon to be inserted by said applicator; said inner tube having a forward and rearward end corresponding to said forward and rearward end of said outer tube when mated;
   said outer tube having at least one shoulder and said inner tube having at least one slot engageable with said shoulder, said shoulder designed to support the tampon after the tampon is placed in said inserter; and
   said inner tube having a radially compressible means consisting of a pair of flanges and a pair of inward and downwardly tapering slots at either side of said flanges, said slots having stops located near the rearward edge of the inner tube.

* * * * *